United States Patent
Shekalim et al.

(10) Patent No.: US 11,844,935 B2
(45) Date of Patent: *Dec. 19, 2023

(54) COVER FOR LIQUID DELIVERY SYSTEM WITH INTEGRATED PLUNGER POSITION SENSING USING FOCUSED OPTICAL BEAM AND LINEAR POTENTIOMETER

(71) Applicant: PATIENTS PENDING LTD., London (GB)

(72) Inventors: Avraham Shekalim, Nesher (IL); Noam Peleg, Gan Ner (IL)

(73) Assignee: PATIENTS PENDING LTD., London (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/067,263

(22) Filed: Dec. 16, 2022

(65) Prior Publication Data
US 2023/0117367 A1  Apr. 20, 2023

Related U.S. Application Data

(63) Continuation of application No. 16/954,998, filed as application No. PCT/IL2017/051356 on Dec. 18, 2017, now Pat. No. 11,529,471.

(51) Int. Cl.
*A61M 5/315* (2006.01)
*A61M 5/32* (2006.01)
(Continued)

(52) U.S. Cl.
CPC ...... *A61M 5/31568* (2013.01); *A61M 5/3202* (2013.01); *G01B 7/14* (2013.01);
(Continued)

(58) Field of Classification Search
CPC ............ A61M 5/31568; A61M 5/3202; A61M 5/31525; A61M 2005/3126;
(Continued)

(56) References Cited

U.S. PATENT DOCUMENTS

| 5,006,110 A | 4/1991 | Garrison et al. |
| 5,792,117 A * | 8/1998 | Brown ...................... G01F 3/16 604/207 |

(Continued)

FOREIGN PATENT DOCUMENTS

| EP | 0319277 | 6/1989 |
| EP | 2879740 | 3/2017 |

(Continued)

OTHER PUBLICATIONS

International Search Report and Written Opinion of PCT/IL2017/051356, dated Mar. 26, 2018, 7 pages.
(Continued)

*Primary Examiner* — Dung T Ulsh
(74) *Attorney, Agent, or Firm* — Hamre, Schumann, Mueller & Larson, P.C.

(57) ABSTRACT

A sliding cover for a liquid delivery device, such as a cap (100) for a pen injector (200), incorporates a set of sensors including an optical sensor (110) with an output which changes during uncapping or capping motions on passing of a plunger (220) of the pen injector. This output is used together with a position sensor (120) to determine the position of the plunger along a cylinder (210) of the liquid delivery device. By monitoring changes in the plunger position, the quantity of dosages delivered by the liquid delivery device can be determined, displayed, stored and/or transmitted to an external device for further data processing or storage. Preferred implementations of the invention employ optical sensors with a converging beam (115), and/or position sensors employing linear potentiometer strips (132).

20 Claims, 15 Drawing Sheets

(51) Int. Cl.
*G01B 7/14* (2006.01)
*G01V 8/12* (2006.01)

(52) U.S. Cl.
CPC ....... *G01V 8/12* (2013.01); *A61M 2205/3306* (2013.01); *A61M 2205/3327* (2013.01); *A61M 2205/502* (2013.01); *A61M 2205/52* (2013.01)

(58) Field of Classification Search
CPC .. A61M 2205/3306; A61M 2205/3327; A61M 2205/502; A61M 2205/52; A61M 2205/332; A61M 2205/3379; G01D 5/26; G01F 11/029
See application file for complete search history.

(56) References Cited

U.S. PATENT DOCUMENTS

| | | | |
|---|---|---|---|
| 8,743,662 B2 | 6/2014 | Sjölund et al. | |
| 8,817,258 B2 | 8/2014 | Whalley et al. | |
| 10,384,014 B2 * | 8/2019 | Forlani | A61M 5/1684 |
| 2013/0310756 A1 * | 11/2013 | Whalley | A61M 5/24 |
| | | | 604/189 |
| 2014/0288422 A1 * | 9/2014 | Brady | A61M 5/007 |
| | | | 600/432 |
| 2015/0018775 A1 | 1/2015 | Groeschke et al. | |
| 2015/0025502 A1 | 1/2015 | Spenser et al. | |
| 2016/0136353 A1 | 5/2016 | Adams | |
| 2017/0056603 A1 | 3/2017 | Cowan et al. | |

FOREIGN PATENT DOCUMENTS

| | | |
|---|---|---|
| WO | 2008/113772 | 9/2008 |
| WO | 2013/176770 | 11/2013 |
| WO | 2017/009724 | 1/2017 |

OTHER PUBLICATIONS

The extended European search report issued for European patent application No. 17935601.9, dated Jun. 22, 2021, 8 pages.

\* cited by examiner

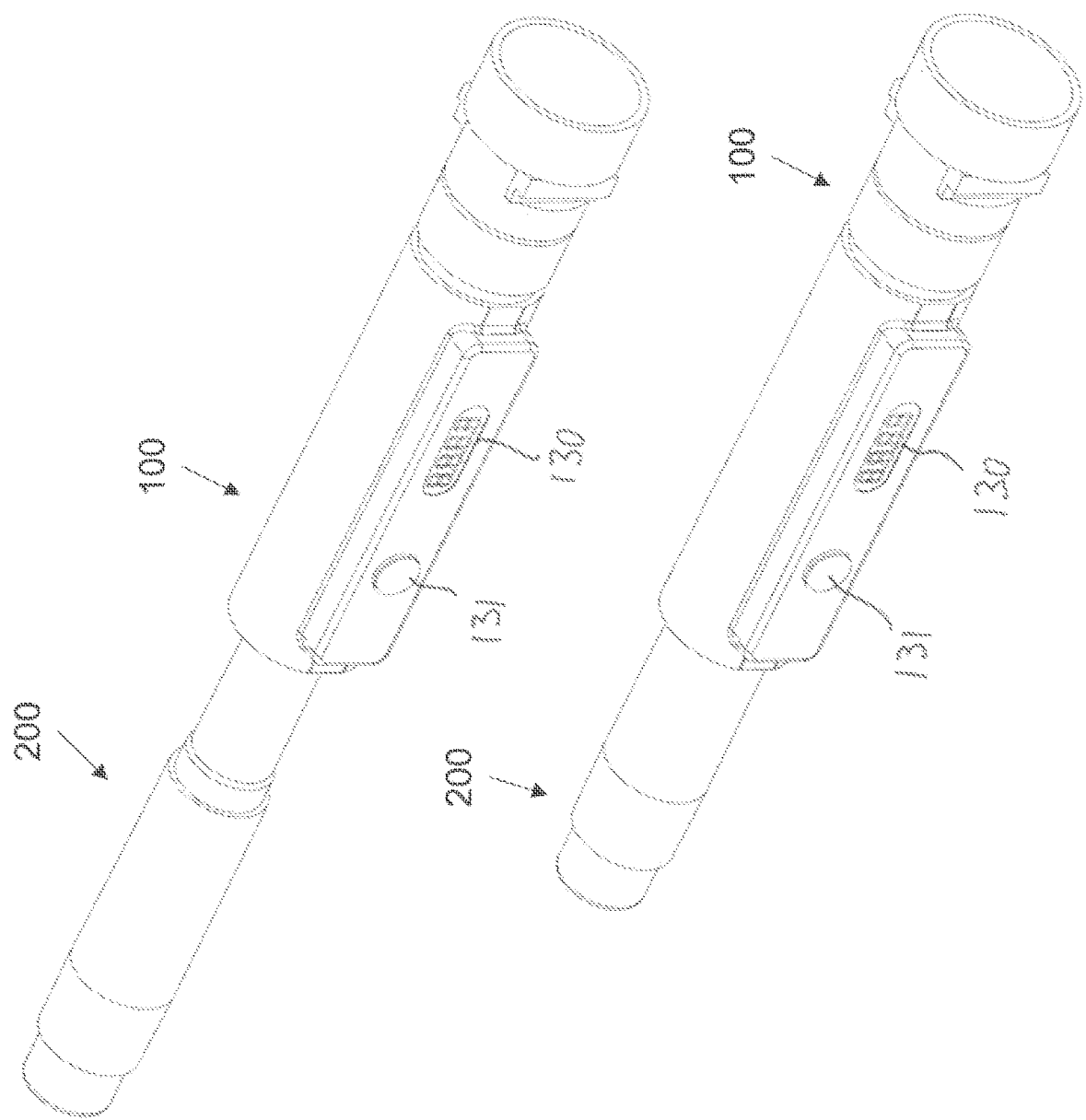

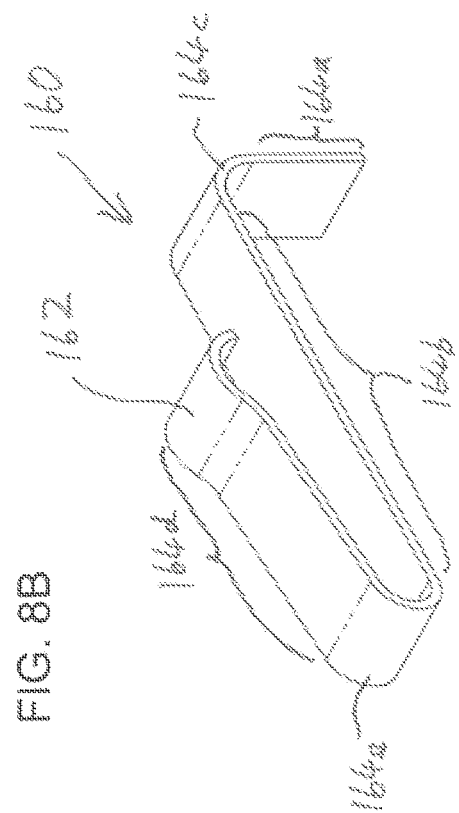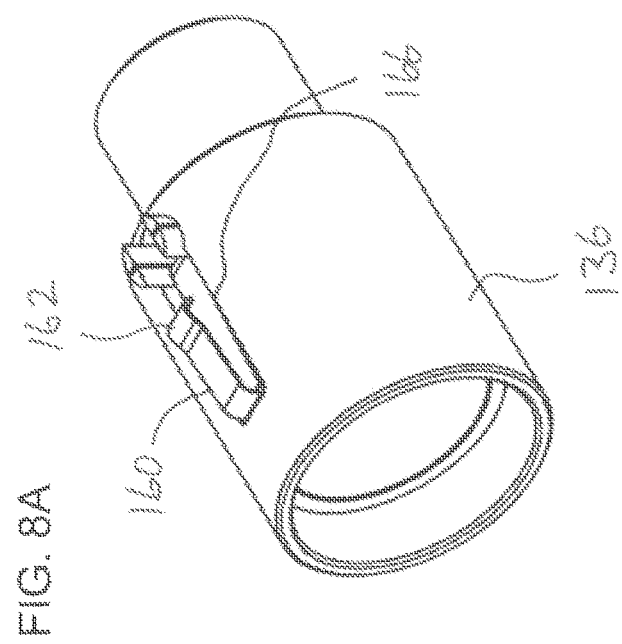

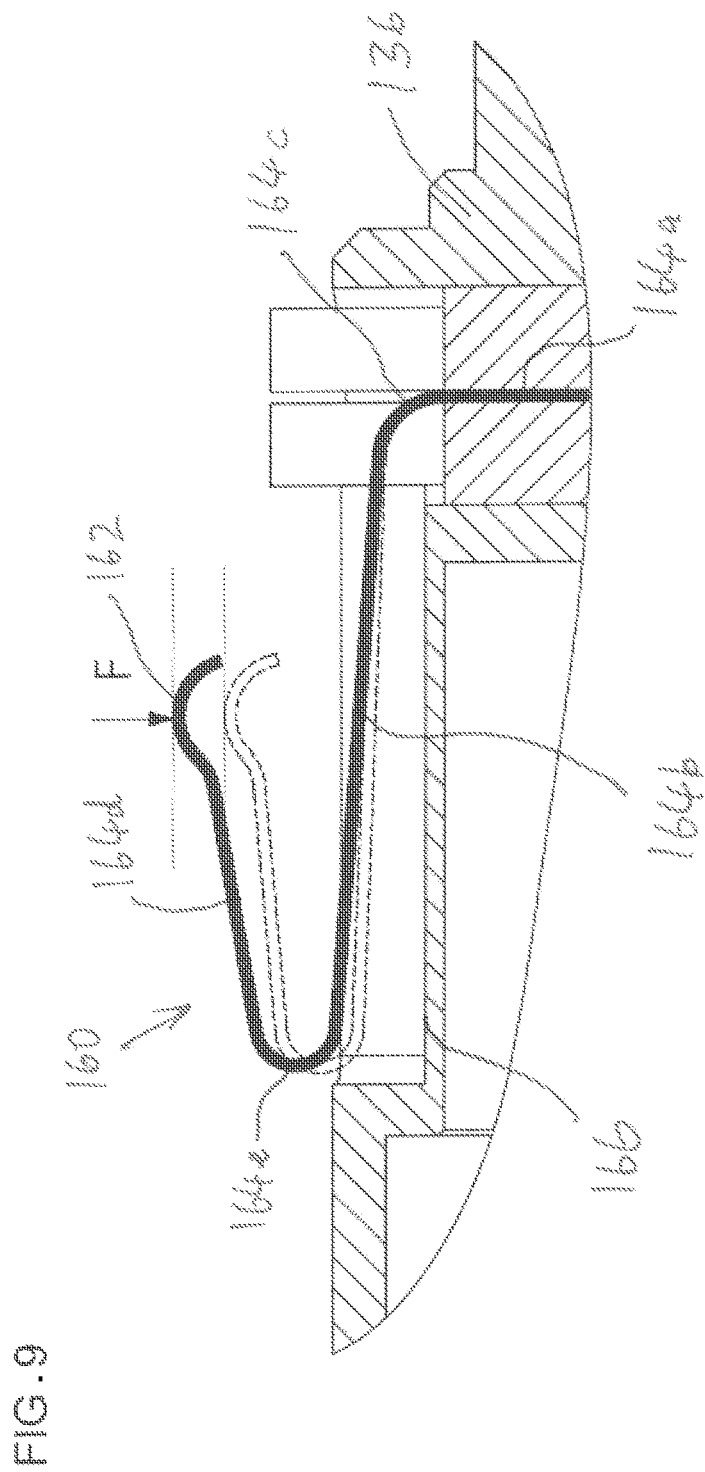

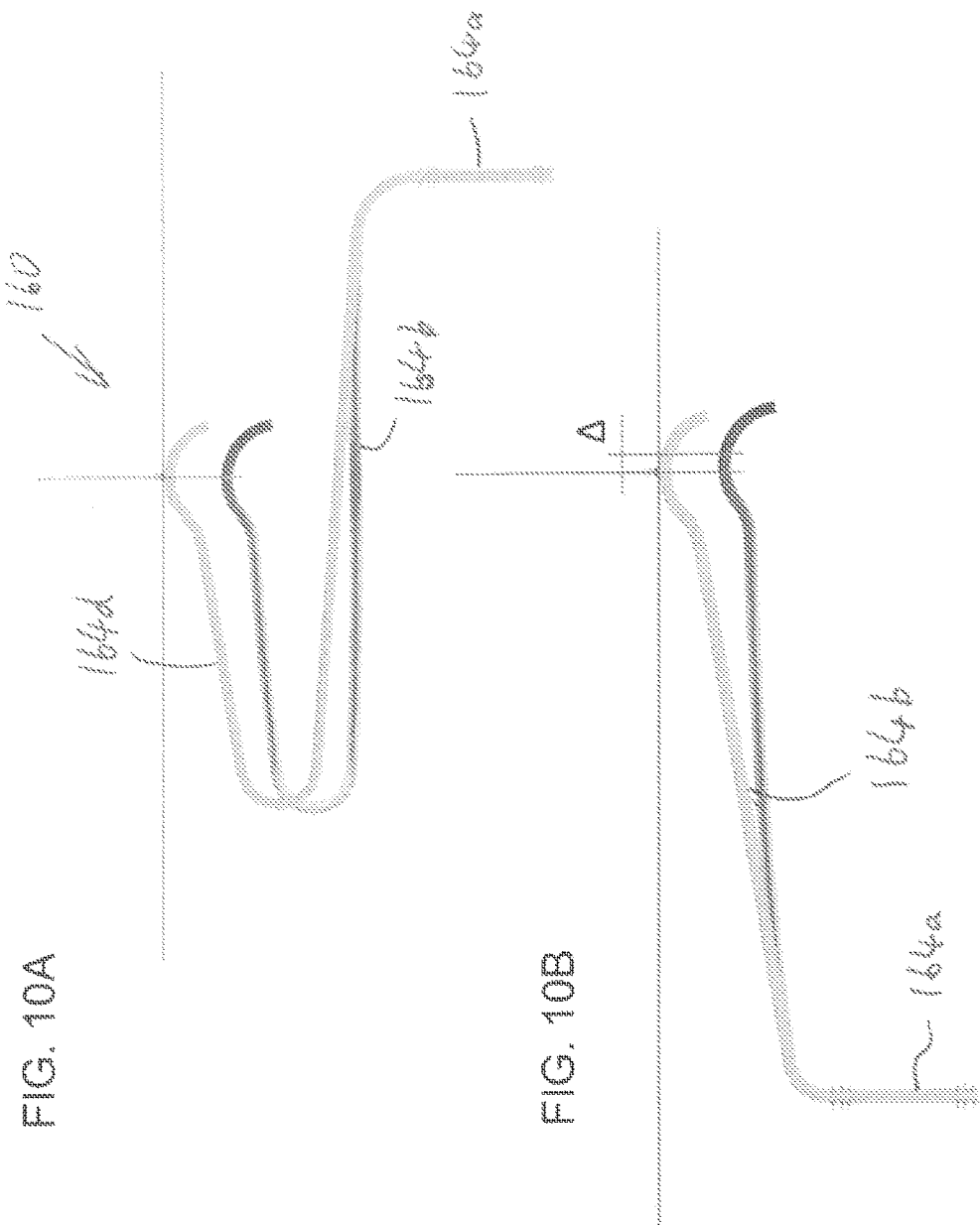

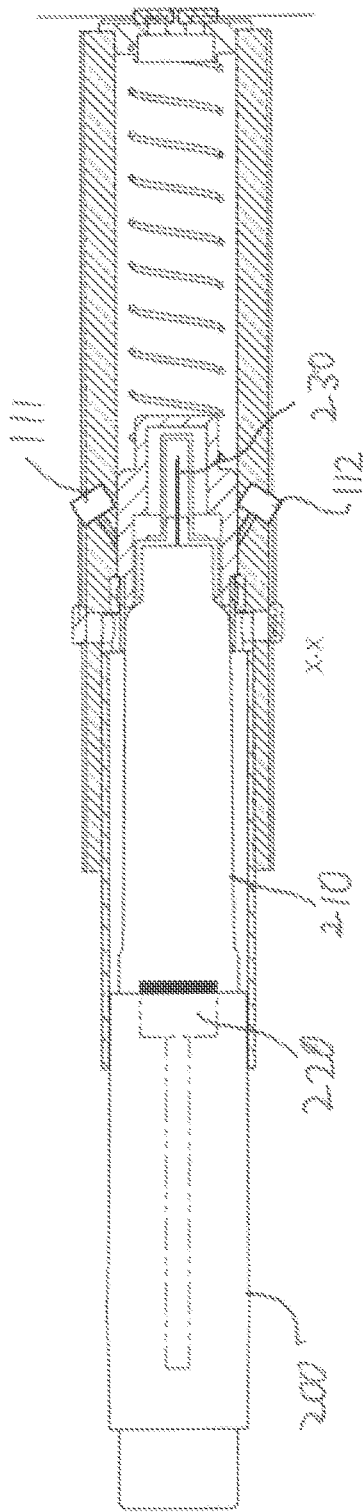
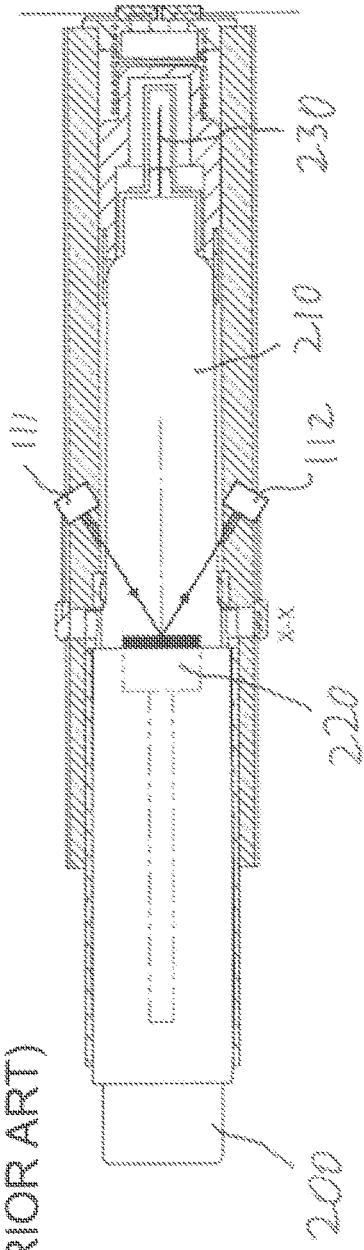
FIG. 11A (PRIOR ART)
FIG. 11B (PRIOR ART)

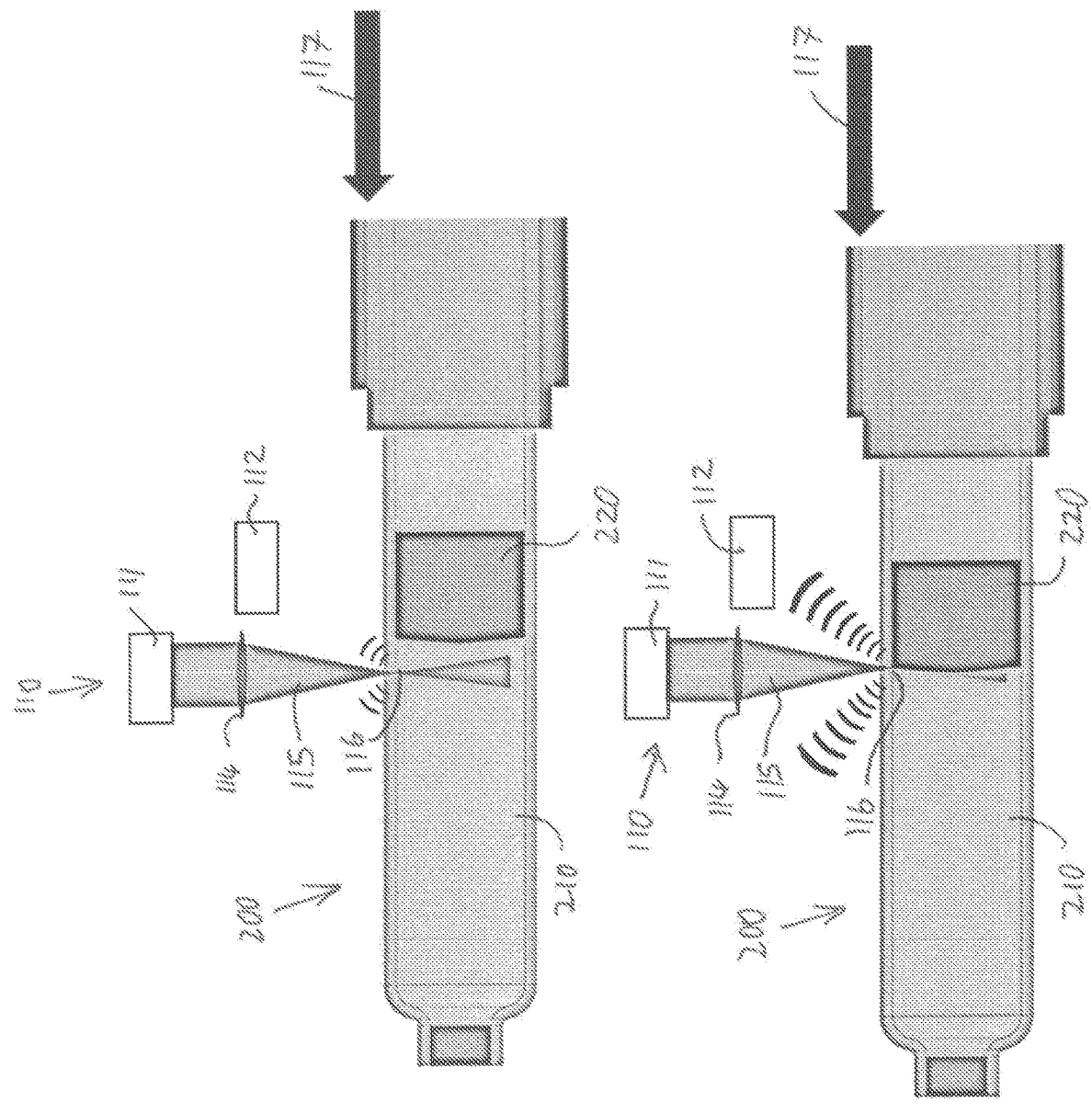

COVER FOR LIQUID DELIVERY SYSTEM WITH INTEGRATED PLUNGER POSITION SENSING USING FOCUSED OPTICAL BEAM AND LINEAR POTENTIOMETER

FIELD AND BACKGROUND OF THE INVENTION

The present invention relates to liquid delivery systems, apparatuses, and methods and, in particular, it concerns techniques for measuring the timing and quantity of doses delivered by a pen-injector type drug delivery device and/or monitoring the quantity of drug remaining in the device.

In the field of liquid delivery devices, and particularly pen injectors, there is a need to provide the user with reliable information regarding previously administered doses of a liquid drug.

Various attempts have been made to add functionality to pen injectors by providing a smart cap. By way of example, U.S. Pat. No. 8,743,662, coassigned with the present invention, discloses a smart cap for a pen injector which monitors the time which has elapsed since a previous use of the pen injector.

Other smart cap devices have attempted to measure the quantity of a drug dose dispensed. One example of such a device is U.S. Pat. No. 8,817,258.

An improvement to the above devices is described in PCT Patent Application Publication No. WO 2017/009724 A1, coassigned with the present invention, which is hereby incorporated by reference as if set out entirely herein. This application discloses a smart cap for a pen injector which detects a quantity of a drug remaining in the pen injector by sensing plunger position.

SUMMARY OF THE INVENTION

The present invention includes apparatuses, methods, and systems that include an apparatus in which sensors are integrated with a sliding cover of a liquid delivery system. In some cases, the apparatus can measure the position of a plunger of the liquid delivery system while the cover is being removed or replaced.

According to the teachings of an embodiment of the present invention there is provided, an apparatus for use with a liquid delivery system, the liquid delivery system including a transparent cylinder for housing a liquid and an at least partially opaque plunger movable along an axis of the cylinder for expelling the liquid through an outlet, the apparatus comprising: (a) a sliding cover configured for sliding engagement with the cylinder so as to be slidable along the cylinder parallel to the axis from a first position to a second position; (b) a set of sensors housed in the sliding cover so as to move together with the sliding cover, the set of sensors comprising: (i) an optical sensor having an optical emitter for emitting radiation and an optical receiver for generating a first output indicative of an amount of the radiation received by the optical receiver, the optical sensor further comprising a focusing element deployed in relation to the optical emitter so as to generate a converging beam of radiation converging towards a focal point, the converging beam being directed inwards, and (ii) a position sensor deployed for generating a second output indicative of a current position of the sliding cover between the first position and the second position; and (c) a processing system associated with the set of sensors so as to receive at least the first output and the second output, the processing system being configured to be responsive to a variation in the first output indicative of the optical sensor reaching a known spatial relationship to the plunger to determine a corresponding current position of the sliding cover as indicated by the second output, and thereby to determine a location of the plunger along the cylinder.

According to a further feature of an embodiment of the present invention, the optical sensor directs the converging beam obliquely inwards.

According to a further feature of an embodiment of the present invention, the focusing element comprises a refractive lens.

According to a further feature of an embodiment of the present invention, the optical emitter and the focusing element are deployed such that the converging beam reaches the focal point after traversing a majority of a width of the transparent cylinder.

According to a further feature of an embodiment of the present invention, the focal point lies at or near a wall of the transparent cylinder.

According to a further feature of an embodiment of the present invention, the sliding cover is implemented as a cap with a central bore for receiving an end portion of a pen injector having a projecting needle.

According to a further feature of an embodiment of the present invention, there is also provided a cradle slidingly mounted within the central bore, the cradle configured for receiving the end portion of the pen injector, the cradle being spring biased towards an end position for engaging the end portion of the pen injector when the sliding cover is in the first position, and being retractable to move together with the end portion of the pen injector as the sliding cover slides to the second position.

According to a further feature of an embodiment of the present invention, the position sensor is associated with the cradle so that the second output is indicative of a current position of the cradle within the central bore.

According to a further feature of an embodiment of the present invention, the position sensor comprises a linear potentiometer strip deployed within the cap so as to extend parallel to the axis, and a pressure element mounted to the cradle and biased so as to press against the linear potentiometer strip.

According to a further feature of an embodiment of the present invention, the pressure element comprises a spring-loaded ball.

According to an alternative further feature of an embodiment of the present invention, the pressure element comprises a leaf spring mounted to the cradle, the leaf spring providing a protuberance deployed so as to press against the linear potentiometer strip.

According to a further feature of an embodiment of the present invention, the leaf spring is implemented as a folded cantilever leaf spring.

According to a further feature of an embodiment of the present invention, the folded cantilever leaf spring comprises a first elongated segment anchored to the cradle, and a second elongated segment connected to the first elongated segment via a bend region, wherein the protuberance is provided on the second elongated segment, the first and second elongated segments and the bend region being configured so accommodate radial displacement of the protuberance towards the cradle without generating axial displacement of the protuberance relative to the cradle.

According to a further feature of an embodiment of the present invention, there is also provided a non-volatile data storage component associated with the processing system, and wherein the processing system is configured to store a previous location of the plunger, compare a current location of the plunger to the previous location, determine whether liquid has been dispensed, and to calculate a quantity of the liquid that has been dispensed.

According to a further feature of an embodiment of the present invention, there is also provided a display integrated with the sliding cover, wherein the processing system is further configured to display data relating to a delivered dosage.

According to a further feature of an embodiment of the present invention, there is also provided a wireless communication subsystem associated with the processing system and configured for transmitting data to an external device.

According to a further feature of an embodiment of the present invention, a pen injector configured for delivering measured doses of a liquid drug via a needle, and wherein the sliding cover is implemented as a cap with a central bore for receiving an end portion of the pen injector including the needle.

There is also provided according to the teachings of an embodiment of the present invention, an apparatus for use with a pen injector, the pen injector including a transparent cylinder for housing a liquid and an at least partially opaque plunger movable along an axis of the cylinder for expelling the liquid through an outlet, the apparatus comprising: (a) a cap with a bore extending along an axis, the cap configured for sliding engagement with the cylinder so as to be slidable along the cylinder parallel to the axis from a first position to a second position; (b) a cradle slidingly mounted within the central bore, the cradle configured for receiving an end portion of the pen injector, the cradle being spring biased towards an end position for engaging the end portion of the pen injector when the cap is in the first position, and being retractable to move together with the end portion of the pen injector as the cap slides to the second position; (c) a set of sensors housed in the cap so as to move together with the cap, the set of sensors comprising: (i) an optical sensor having an optical emitter for emitting radiation and an optical receiver for generating a first output indicative of an amount of the radiation received by the optical receiver, and (ii) a position sensor deployed for generating a second output indicative of a current position of the cradle within the central bore; and (d) a processing system associated with the set of sensors so as to receive at least the first output and the second output, the processing system being configured to be responsive to a variation in the first output indicative of the optical sensor reaching a known spatial relationship to the plunger to determine a corresponding current position of the cradle as indicated by the second output, and thereby to determine a location of the plunger along the cylinder, wherein the position sensor comprises a linear potentiometer strip deployed within the cap so as to extend parallel to the axis, and a pressure element mounted to the cradle and biased so as to press against the linear potentiometer strip.

According to a further feature of an embodiment of the present invention, the pressure element comprises a spring-loaded ball.

According to a further feature of an embodiment of the present invention, the pressure element comprises a leaf spring mounted to the cradle, the leaf spring providing a protuberance deployed so as to press against the linear potentiometer strip.

According to a further feature of an embodiment of the present invention, the leaf spring is implemented as a folded cantilever leaf spring.

According to a further feature of an embodiment of the present invention, the folded cantilever leaf spring comprises a first elongated segment anchored to the cradle, and a second elongated segment connected to the first elongated segment via a bend region, wherein the protuberance is provided on the second elongated segment, the first and second elongated segments and the bend region being configured so accommodate radial displacement of the protuberance towards the cradle without generating axial displacement of the protuberance relative to the cradle.

According to a further feature of an embodiment of the present invention, the optical sensor further comprises a focusing element deployed in relation to the optical emitter so as to generate a converging beam of radiation converging towards a focal point, the converging beam being directed obliquely inwards.

According to a further feature of an embodiment of the present invention, the focusing element comprises a refractive lens.

According to a further feature of an embodiment of the present invention, the optical emitter and the focusing element are deployed such that the converging beam reaches the focal point after traversing a majority of a width of the transparent cylinder.

According to a further feature of an embodiment of the present invention, the focal point lies at or near a wall of the transparent cylinder.

According to a further feature of an embodiment of the present invention, there is also provided a non-volatile data storage component associated with the processing system, and wherein the processing system is configured to store a previous location of the plunger, compare a current location of the plunger to the previous location, determine whether liquid has been dispensed, and to calculate a quantity of the liquid that has been dispensed.

According to a further feature of an embodiment of the present invention, there is also provided a display integrated with the cap, wherein the processing system is further configured to display data relating to a delivered dosage.

According to a further feature of an embodiment of the present invention, there is also provided a wireless communication subsystem associated with the processing system and configured for transmitting data to an external device.

According to a further feature of an embodiment of the present invention, there is also provided a pen injector configured for delivering measured doses of a liquid drug via a needle, an end portion of the pen injector cooperating with the cradle and being received within the bore of the cap.

BRIEF DESCRIPTION OF THE DRAWINGS

The invention is herein described, by way of example only, with reference to the accompanying drawings, wherein:

FIGS. 2A-2C are schematic isometric views of the cap and pen injector of FIG. 1 with the pen injector outside, partially inserted, and fully inserted into the cap, respectively;

FIG. 8A is an isometric view of a cradle and leaf spring assembly from the cap of FIG. 7A;

FIG. 8B is an enlarged isometric view of the leaf spring from the assembly of FIG. 8A;

FIG. 9 is a partial cross-sectional view taken through a central axis of the assembly of FIG. 8A bisecting the leaf spring, illustrating in dashed lines a deflected form of the leaf spring;

FIGS. 10A and 10B are illustrations derived from finite elements analysis indicating the geometrical changes occurring to the leaf spring of FIG. 8B and to an alternative cantilever leaf spring, respectively, under an applied load;

FIGS. 11A and 11B are cross-sectional views corresponding to FIGS. 7A and 7B, respectively, of PCT Patent Application Publication No. WO 2017/009724 A1;

FIGS. 15A and 15B are two views similar to FIG. 12 illustrating an alternative implementation of an optical sensor according to an aspect of the present invention, the liquid delivery system being shown in two positions relative to the components of the optical sensor.

DESCRIPTION OF THE PREFERRED EMBODIMENTS

Figure 1:
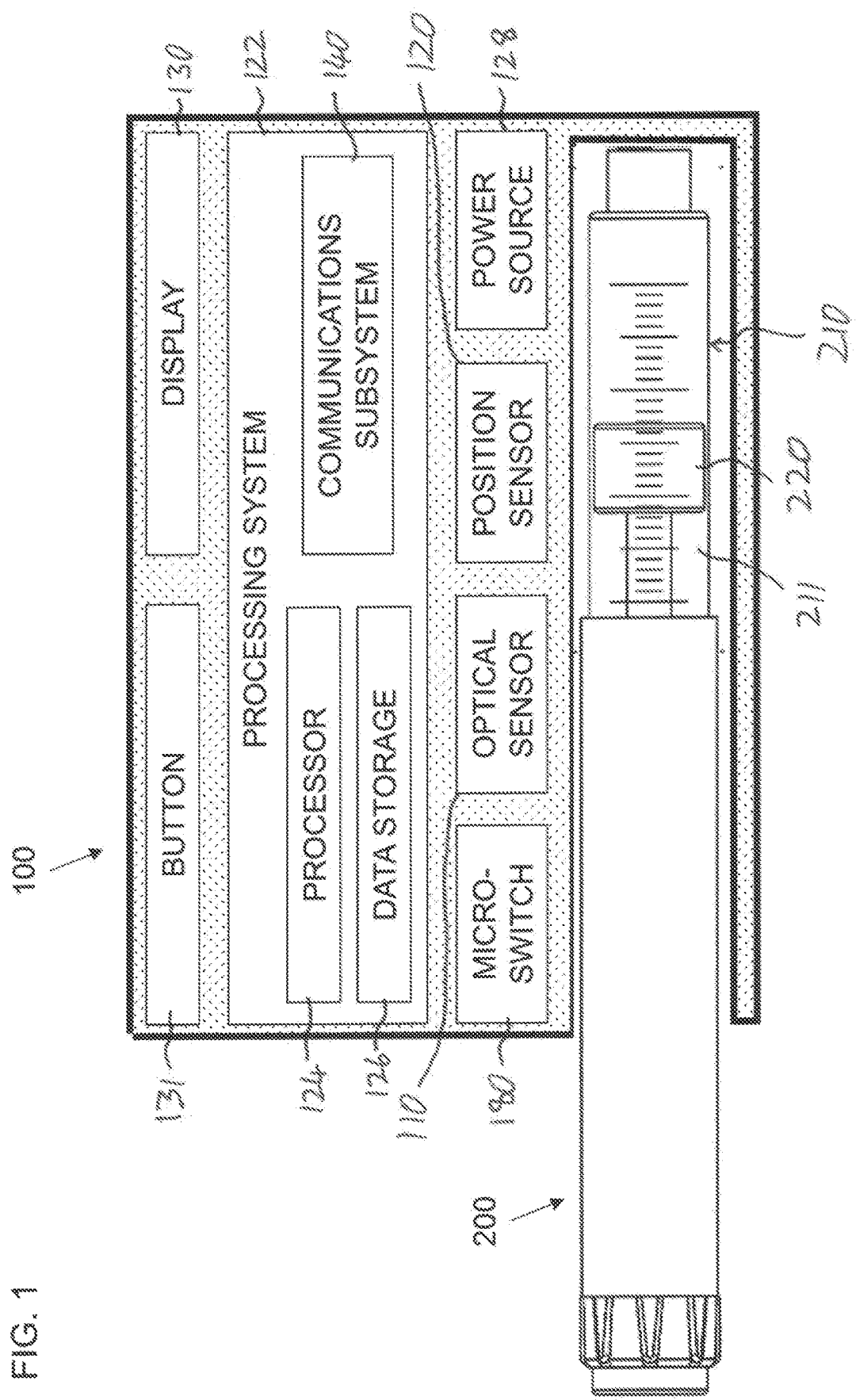
FIG. 1 is a schematic representation of a cap, constructed and operative according to an embodiment of the present invention, in use for capping a pen injector.

The present invention includes apparatuses, methods, and systems that include an apparatus in which sensors are integrated with a sliding cover of a liquid delivery system and measure the position of a plunger of the liquid delivery system. In some cases, the sliding cover can measure the position of a plunger while the cover is being removed or replaced.

The principles and operation of an apparatus according to the present invention may be better understood with reference to the drawings and the accompanying description.

INTRODUCTION

By way of introduction, in general terms, the present invention employs a sliding cover, such as a cap 100, for a liquid delivery system, such as a pen injector 200. The sliding cover incorporates a set of sensors including at least one optical sensor 110 which operates during an un-capping and/or capping motion of the cap to generate a signal which changes as the optical sensor 110 reaches a plunger 220 of the liquid delivery device. This signal is then used together with an output of a position sensor 120 to determine the position of plunger 220 along a cylinder 210 of the liquid delivery device. By monitoring changes in the plunger position, the quantity of dosages delivered by the liquid delivery device can be determined, displayed, stored and/or transmitted to an external device for further data processing or storage.

Thus, in general terms, the drawings illustrate various features of an apparatus, constructed and operative according to an embodiment of the present invention, implemented as a cap 100 for an injection pen ("pen injector") 200, where pen injector 200 has a generally transparent reservoir in the form of a cylinder 210 with a transparent wall 211 for housing a liquid, and an at least partially opaque plunger 220 (interchangeably referred to herein as "piston" 220) movable along an axis of cylinder 210 for expelling the liquid through an outlet, typically implemented as a septum associated with an interchangeable injection needle 230.

Figure 2A:
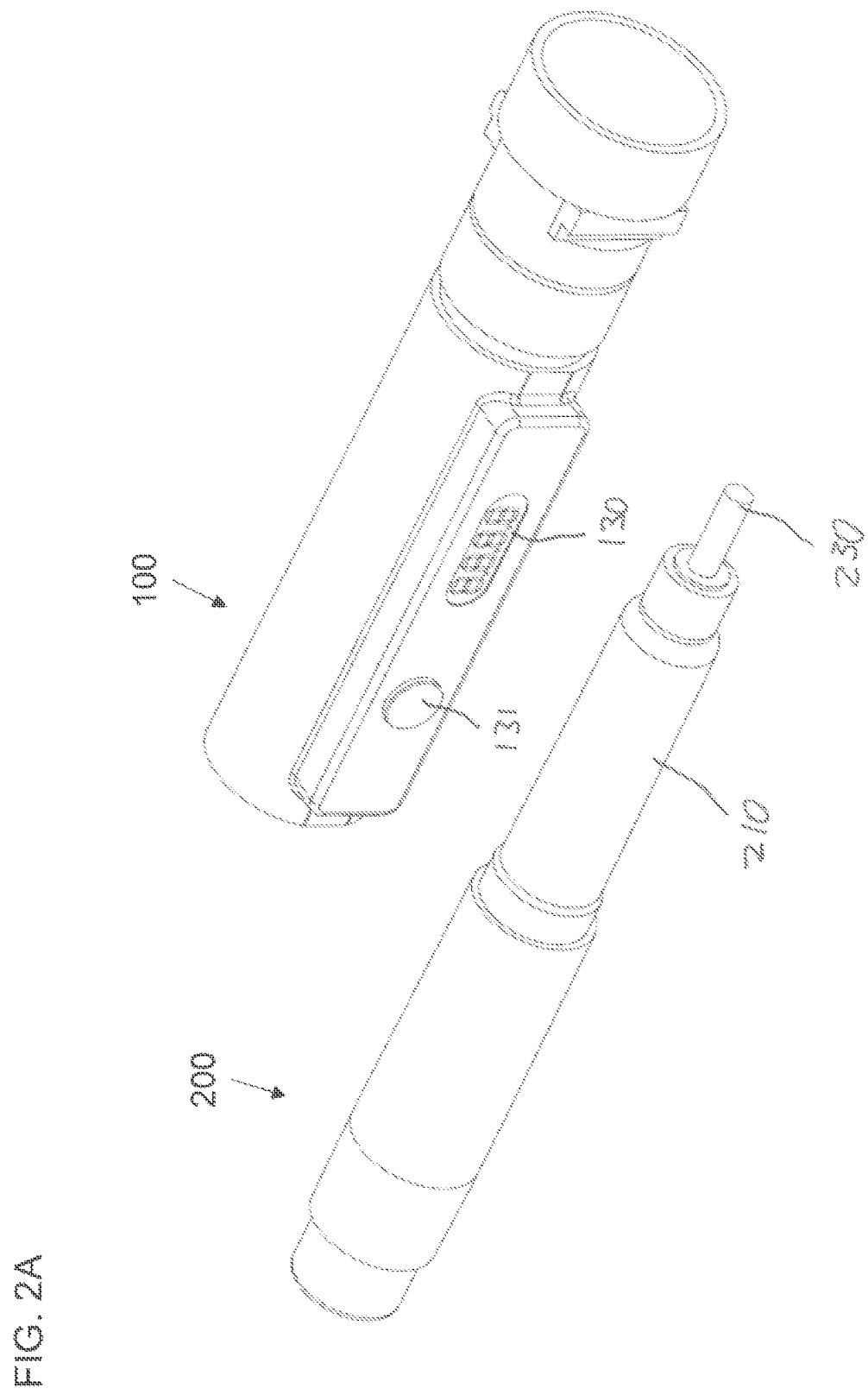

The apparatus is formed as a sliding cover, here a cap 100, configured for sliding engagement with cylinder 210 so as to be slidable along the cylinder parallel to the axis from a first position (FIG. 2B), at the beginning of recapping, to a second position (FIG. 2C) in which the cap is fully engaged with pen injector 200.

A set of sensors is housed in the sliding cover so as to move together with the sliding cover. The set of sensors includes an optical sensor 110 having an optical emitter 111 for emitting radiation and an optical receiver 112 for generating a first output indicative of an amount of the radiation received by the optical receiver. Optical sensor 110 is deployed in inward-facing deployment such that, when the sliding cover slides in engagement with transparent cylinder 210, the first output changes as optical sensor 110 passes plunger 220.

Also included in the set of sensors is a position sensor 120 deployed for generating a second output indicative of a current position of sliding cover 100 between the first position and the second position relative to pen injector 200. A processing system 122, including at least one processor 124, is associated with the set of sensors so as to receive the sensor outputs. Processing system 122 is configured to be responsive to a variation in the output from optical sensor 110 indicative of the optical sensor reaching plunger 220 to determine a corresponding current position of cover 100 as indicated by the output of position sensor 120, and thereby to determine a location of plunger 220 along cylinder 210.

A cap according to the generic description presented thus far has been proposed in the aforementioned PCT Patent Application Publication No. WO 2017/009724 A1, for example, as illustrated in FIGS. 11A and 11B, and has been found to provide distinct advantages. Since however accurate determination of an individual dose of medication dispensed from the pen injector requires very accurate determination of plunger position, in some cases to a fraction of a millimeter, there is a need to optimize precision of the sensing systems, both for the optical sensor and for the position sensor. The present invention presents certain particularly preferred implementations of both the position sensor and the optical sensor which are believed to facilitate achieving high-accuracy measurements. Both the optical sensor implementations and the position sensor implementations addressed below are believed to be of utility in their own right, for example, for use together with other sensor arrangements described in the above PCT publication. Certain particularly preferred implementations combine the novel optical sensor configurations with the novel position sensor configuration to achieve particularly advantageous and synergistic results.

Position Sensor

Turning now to FIGS. 3A-10B, these illustrate an implementation of the present invention in which position sensor 120 is implemented using a linear potentiometer strip 132 deployed within cap 100 so as to extend parallel to the axis of capping motion, and a pressure element 134 biased so as to press against the linear potentiometer strip.

Pressure element 134 is mounted to a cradle 136, which is slidingly mounted within a central bore 138 of cap 100. Cradle 136 is configured, typically by being formed with suitably shaped recesses, for receiving an end portion of pen injector 200, and is spring-biased, for example by a helical spring 142, towards an end position (FIG. 3A) for engaging the end portion of pen injector 200 when the cap is in a first position, at the beginning of a capping motion (or the end of an uncapping motion), and being retractable to move together with the end portion of the pen injector as the cap slides to a second, fully-capped position.

The term "cradle" as used here refers to a sliding block, also referred to herein as a "slider", which is shaped to receive the end portion of the pen injector, and preferably accommodates that end portion in a well-defined position independent of whether the pen injector currently has a needle adapter connected, with or without a needle cover, or is needleless with its septum interface exposed. This is preferably achieved by providing engagement features which engage the outer periphery of the front end of the reservoir, radially-outwards from the region of attachment of the needle adapter. The provision of cradle 136 helps to maintain precise alignment of pen injector 200 with cap 100 during motion, ensuring smooth and predictable motion of the pen injector within the cap, and thereby facilitating measurement by linear potentiometer strip 132. The spring loading of cradle 136 ensures that cradle 136 remains engaged with an end portion of pen injector 200 during capping and uncapping, so that an output of the position sensor associated with the cradle is indicative of a current position of the pen injector within the central bore 138.

Figure 3A:
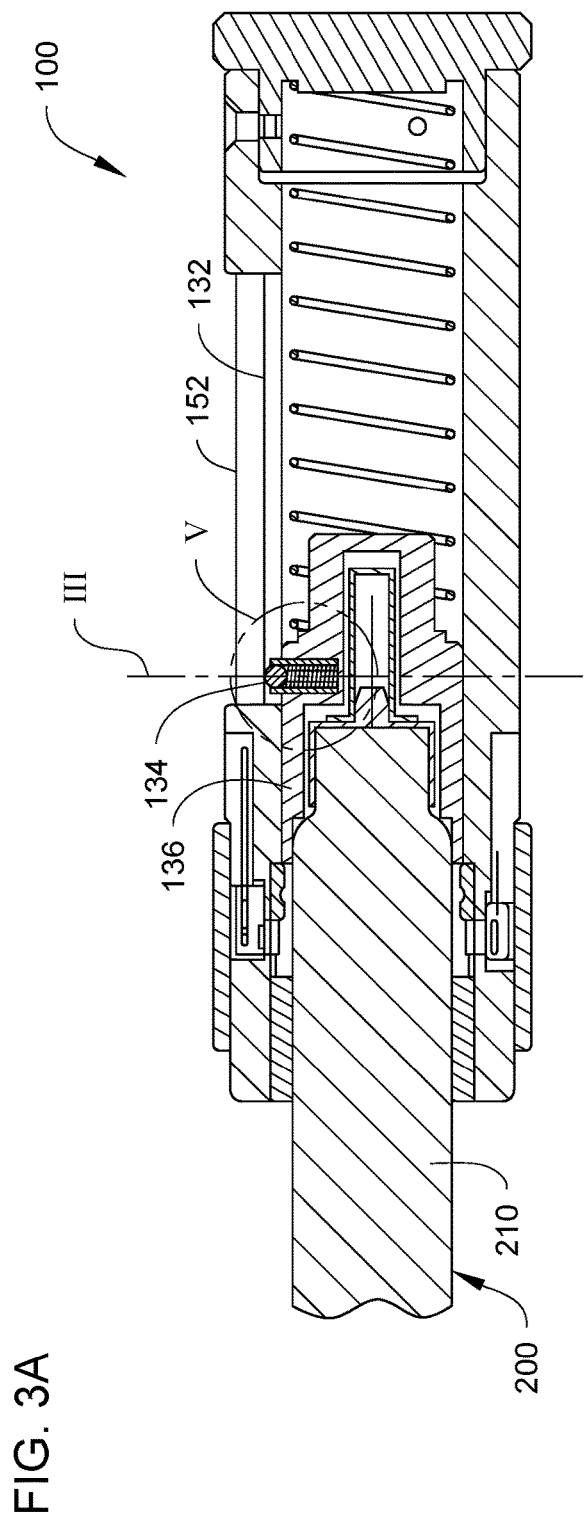
FIG. 3A is a schematic partial cross-sectional view taken through FIG. 2B along a central axis of the cap, illustrating a position sensor according to a first aspect of the present invention.
Figure 3B:
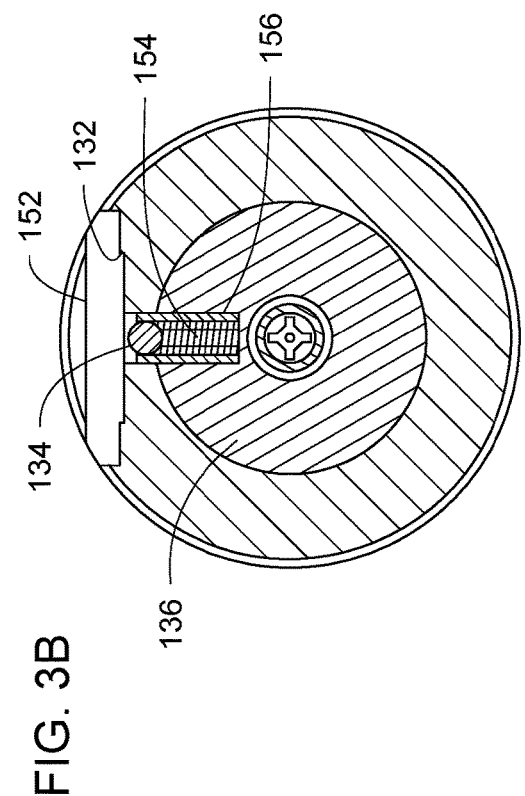
FIG. 3B is a cross-sectional view taken along the dashed line III in FIG. 3A.
Figure 4C:
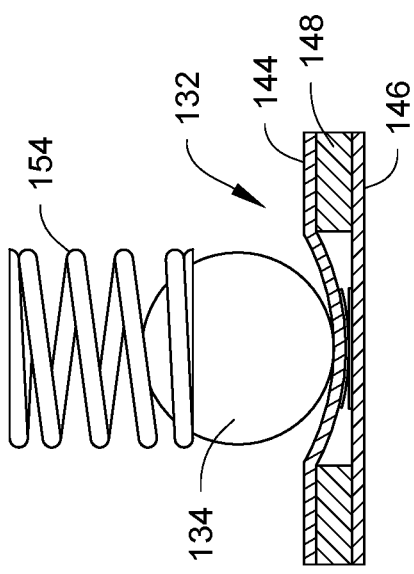
FIG. 4C is a schematic lateral cross-sectional view taken through the linear potentiometer strip of FIG. 4A, illustrating operation of a pressure element on the strip.
Figure 4A:
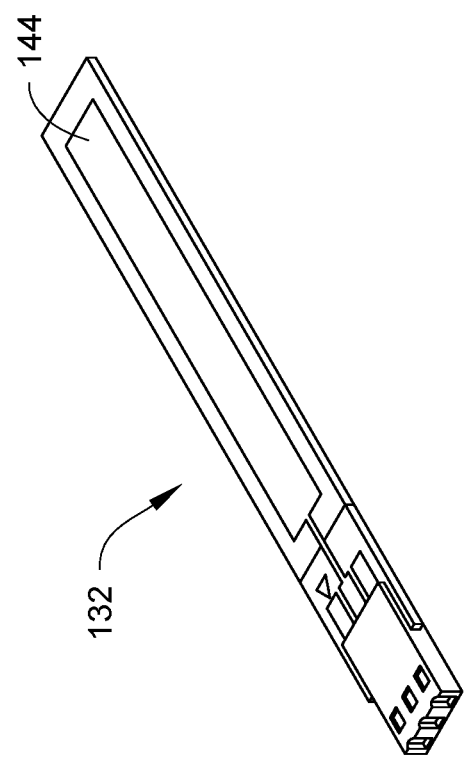
FIG. 4A is a schematic isometric view of a linear potentiometer strip forming part of a position sensor of the cap of FIG. 3A.
Figure 4B:
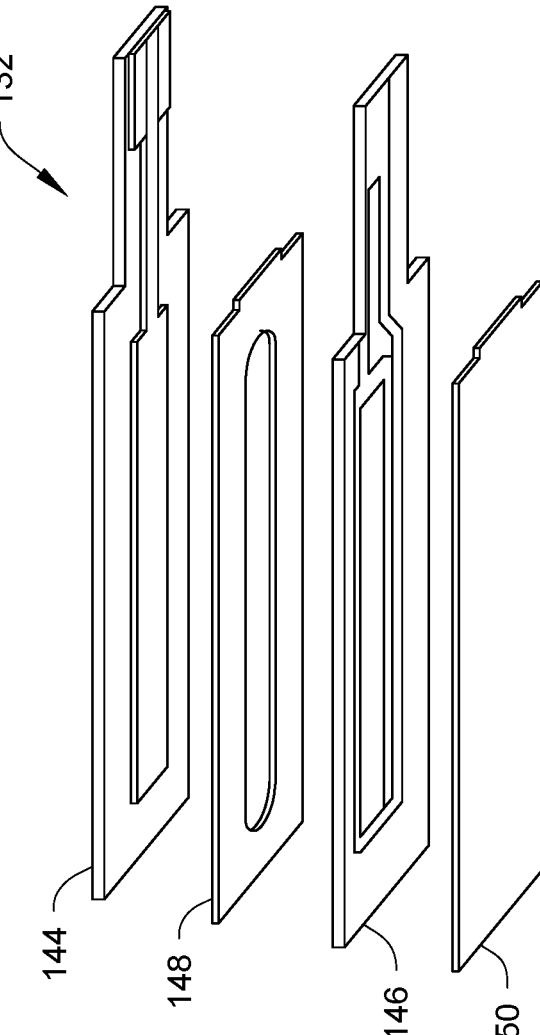
FIG. 4B is a schematic isometric exploded view of the linear potentiometer strip of FIG. 4A.

The term "linear potentiometer strip" is used herein in the description and claims to refer to any strip-like structure with two spaced-apart conductive layers which are selectively brought into contact with each other by localized pressure of a pressure element 134. Such sensors can be "read" in various different modes and using various different electrical arrangements, including a potentiometer mode in which the contact point "reads" an intermediate potential between a high potential and a low potential applied to opposite ends of a first layer via a second conductive layer. An alternative reading arrangement may be determination of a variable resistance between one end of the first layer and the contact point. An exemplary structure for potentiometer strip 132 is shown schematically in FIGS. 4A-4C in which a first layer 144 is the sensing layer or "collector", typically with a single electrical connection, and a second layer 146 is the resistor layer, typically with two contacts for the two ends for applying a voltage along the length of the layer. The first and second layers are spaced apart by an electrically insulating spacer layer 148 which maintains separation between the conductive layers except where pressed upon by a pressure element. An adhesive layer 150 typically attaches the potentiometer strip to an underlying support structure 152 (FIGS. 3A, 3B).

The electrical circuitry required for actuating and reading from the linear potentiometer strip sensor is standard for such sensors, and will not be described here in detail. The circuitry may be provided either as dedicated circuitry integrated with a commercially available off-the-shelf sensor, or may be integrated as part of processing system 122, all as is known in the art.

In the example of FIGS. 3A, 3B, 4C and 5, pressure element 134 is implemented as a spring-loaded ball, biased by a spring 154 along a guide sleeve 156. Spring 154 maintains contact between the ball and the potentiometer strip despite any undulations or other variations in geometry which may occur between the pressure element 134 and the potentiometer strip 132 during the capping (or uncapping) motion.

While the spring-loaded ball implementation is sufficient for many applications, this configuration introduces certain limitations which may limit its performance. Specifically, as illustrated schematically in FIGS. 6A and 6B, potentiometer strip sensors are typically sensitive to variations in contact pressure, since a small contact pressure will typically result in a relatively small area of contact (FIG. 6A) while a larger contact pressure results in a larger area of contact (FIG. 6B). Since measurement typically depends on the extremities of the area of contact, variations in contact pressure typically result in an offset on the position reading. In order to minimize variations in the spring force as spring 154 flexes to compensate for any imprecision in the linear motion of cradle 136, spring 154 is preferably chosen to be relatively long with many turns and a relatively large diameter. However, both the length and the diameter of spring 154 are limited due to design considerations of the cap. Furthermore, in order to allow rolling motion and spring-biased retraction of the spring-loaded ball, some degree of clearance is required between guide sleeve 156 and the ball, resulting in some freedom of lateral motion, and in some cases jamming of the ball against the inner wall of the sleeve, all of which can result in imprecise measurements.

As alternative implementation of a pressure element for use with potentiometer strip 132 is illustrated in FIGS. 7A-10B according to which the pressure element is implemented as a leaf spring 160 mounted to cradle 136. Leaf spring 160 provides a protuberance 162 deployed so as to press against linear potentiometer strip 132. A suitably configured leaf spring has been found to offer relatively constant contact force over the relevant range of displacement, while maintaining minimal axial freedom of motion and a small radial footprint, as will be exemplified below.

In a particularly preferred implementation of leaf spring 160, as best seen in FIGS. 8A and 8B, the leaf spring is implemented as a folded cantilever leaf spring. The term "cantilever leaf spring" is used herein to refer to a leaf spring which is anchored at one region, typically near one end of the spring, and where the active portion carrying protuberance 162 is not otherwise supported. The term "folded" is used to refer to a leaf spring configuration which at least two elongated segments that are interconnected via a bend region, thereby forming a "folded" or "zigzag" shape. One particularly preferred example, as seen in FIG. 8B, includes an anchoring region 164a, typically extending roughly perpendicular to the axis of motion in order to firmly anchor the leaf spring to move together with cradle 136, and a first elongated segment 164b, interconnected to anchoring region 164a via a first bend region 164c. A second elongated segment 164d is connected to first elongated segment 164b via a second bend region 164e. The protuberance 162, typically formed as a convexly curved bulge, is preferably provided on second elongated segment 164d. The entire leaf spring 160 is preferably seated in a corresponding recess 166 formed in cradle 136, with anchoring portion 164a anchored within a corresponding slot formed in the cradle (FIGS. 8A and 9). FIG. 9 illustrates in dashed lines the flexing of leaf spring 160 to accommodate radial displacement of protuberance 162 towards cradle 136.

The use of a folded cantilever form for leaf spring 160 provides particular advantages with regard to isolating radial deflection from axial displacement. This point is best understood by reference to FIGS. 10A and 10B which illustrate forms of deflection for a folded cantilever leaf spring 160 and for an otherwise similar non-folded cantilever leaf spring, respectively. Each drawing shows the spring in an undeflected state and with equal deflections of protuberance 162 perpendicular to the axis of motion, as determined by finite elements analysis.

As seen in FIG. 10B, radial (i.e., up-down as shown) deflection of the non-folded cantilever leaf spring is inherently accompanied by an axial (right-left) displacement A. In contrast, by suitable choice of the lengths and the angles of the first and second elongated segments 164b and 164d, it is possible to implement the folded cantilever leaf spring of FIG. 10A so as to accommodate radial displacement of the protuberance towards the cradle without generating axial displacement of the protuberance relative to the cradle. In this context, radial displacement is referred to as being "without" axial displacement where any residual axial displacement is smaller by at least one, and preferably at least two, orders of magnitude than the radial displacement.

Use of linear potentiometer strip 132 with folded cantilever leaf spring 160 further facilitates achieving particularly high accuracy and reliability of position measurement for the position of pen injector 200 relative to cap 100 during capping and uncapping, thereby facilitating high accuracy operation of the dose measuring and reservoir contents measurement of the present invention as a whole.

Optical Sensor

A further aspect of the present invention relates to enhanced accuracy optical sensing of plunger position compared to various previously disclosed systems. The aforementioned PCT Patent Application Publication No. WO 2017/009724 A1 describes optical sensors in which a beam of light from an emitter 111 is reflected off some region of plunger 220 and the reflected intensity is sensed by a receiver 112. Emitters suitable for such applications are typically various types of LED or laser diode which provide parallel or slightly diverging beams of illuminating light, typically with a significant beam breadth, which may have a width dimension similar to or greater than the required measurement precision. Particularly with the optical sensor geometry of FIGS. 11A and 11B, the variation of the illumination intensity reflected from the plunger varies relatively slowly with plunger position. Even where a radial beam direction is used, the signal detected by the receiver increases over a range of positions of the plunger relative to the cap as the plunger progressively cuts the beam.

In order to enhance the measurement accuracy of the optical sensors of the present invention, according to one particularly preferred aspect of the present invention, optical sensor 110 includes a focusing element 114 deployed in relation to optical emitter 111 so as to generate a converging beam 115 of radiation, preferably converging towards a focal point 116. The use of a focusing element to generate a converging beam facilitates various arrangements of optical sensor 110 which achieve a sharper variation of reflected intensity as a function of plunger position, thereby facilitating more precise overall performance of the apparatus.

Focusing element 114 may be any focusing element which is effective to generate the converging beam 115. One particularly preferred implementation as shown here employs a single refractive lens, although more complex refractive arrangements, and various arrangements of diffractive or reflective optical elements, or any combination thereof, may also be used. The focusing element is formed from material which are suitable for the range of wavelengths of radiation being used, which are typically in the visible or infrared ranges.

Figure 12:
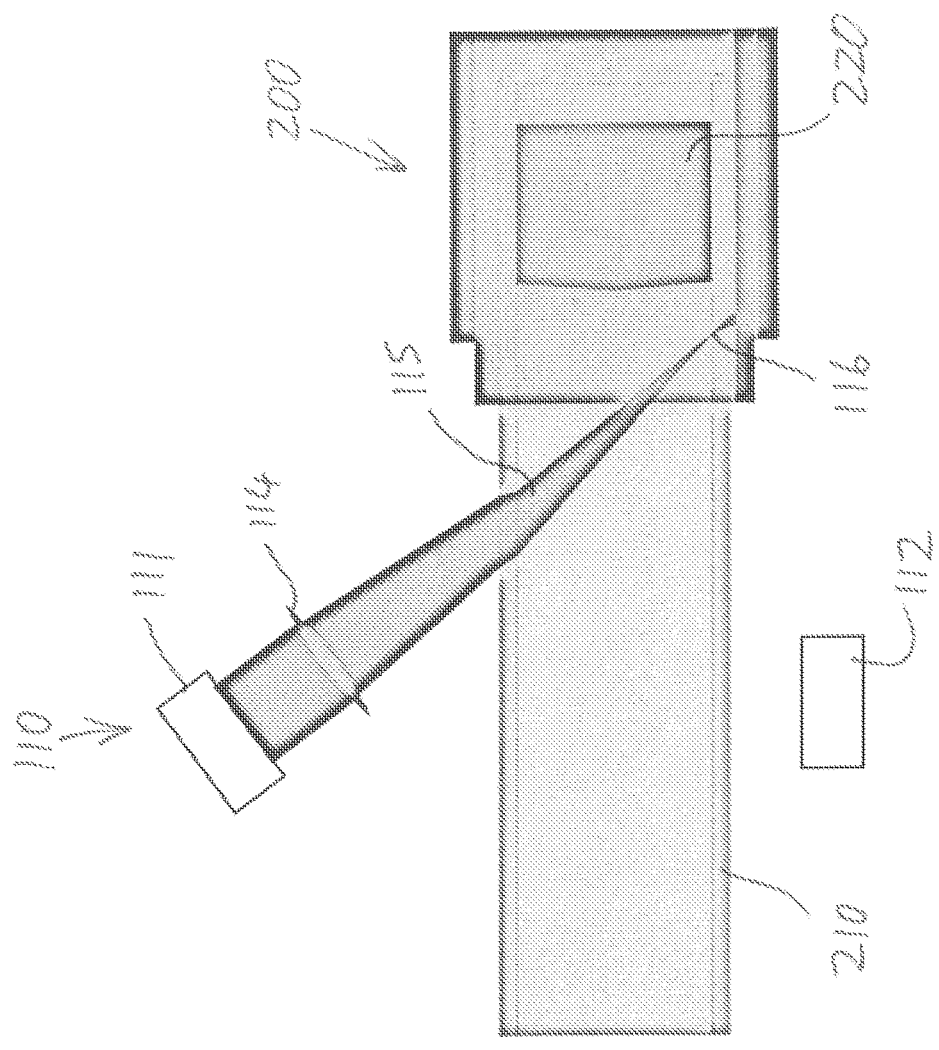
FIG. 12 is a schematic axial cross-sectional view taken through a central axis of a liquid delivery system illustrating the deployment of components of an optical sensor according to a second aspect of the present invention.
Figure 13A:
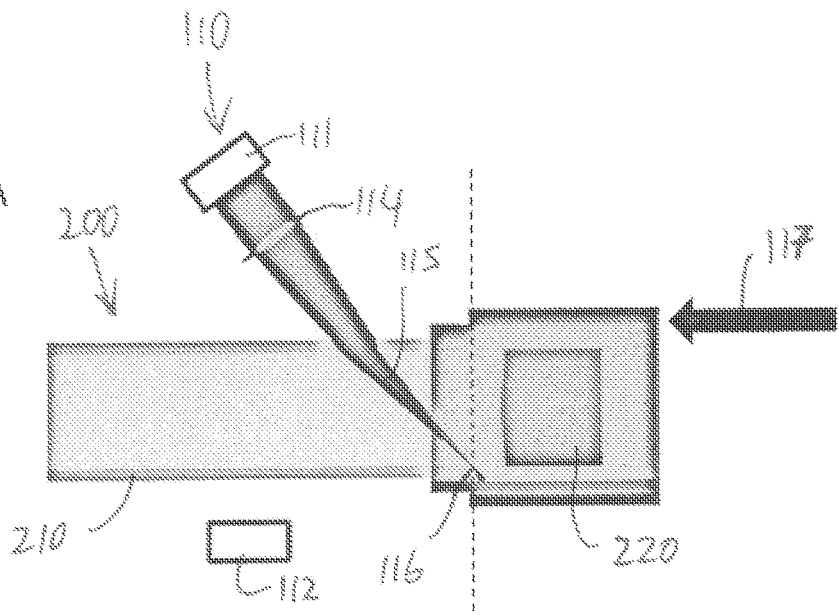
FIGS. 13A-13C are views similar to FIG. 12 illustrating a sequence of positions of the liquid delivery system relative to the components of the optical sensor.
Figure 13B:
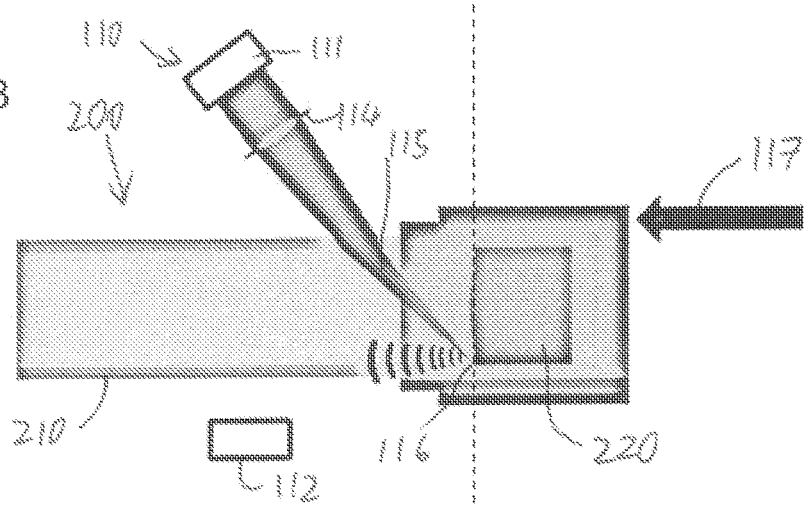
Figure 13C:
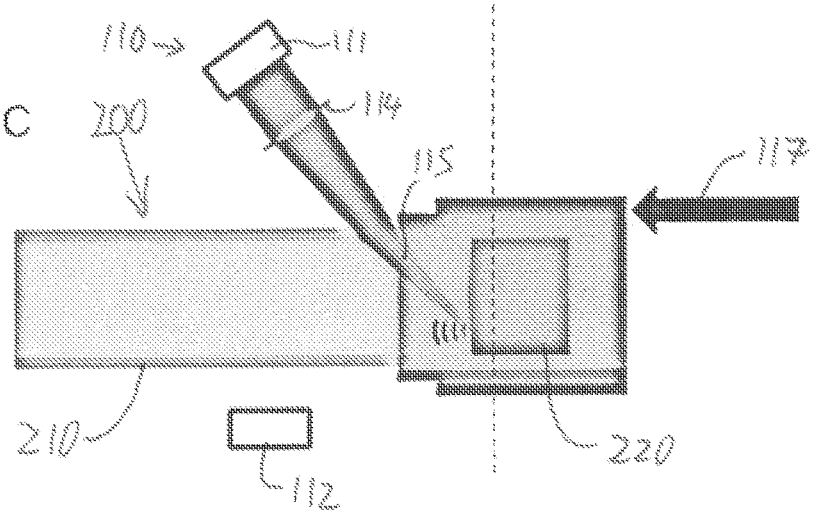
Figure 14:
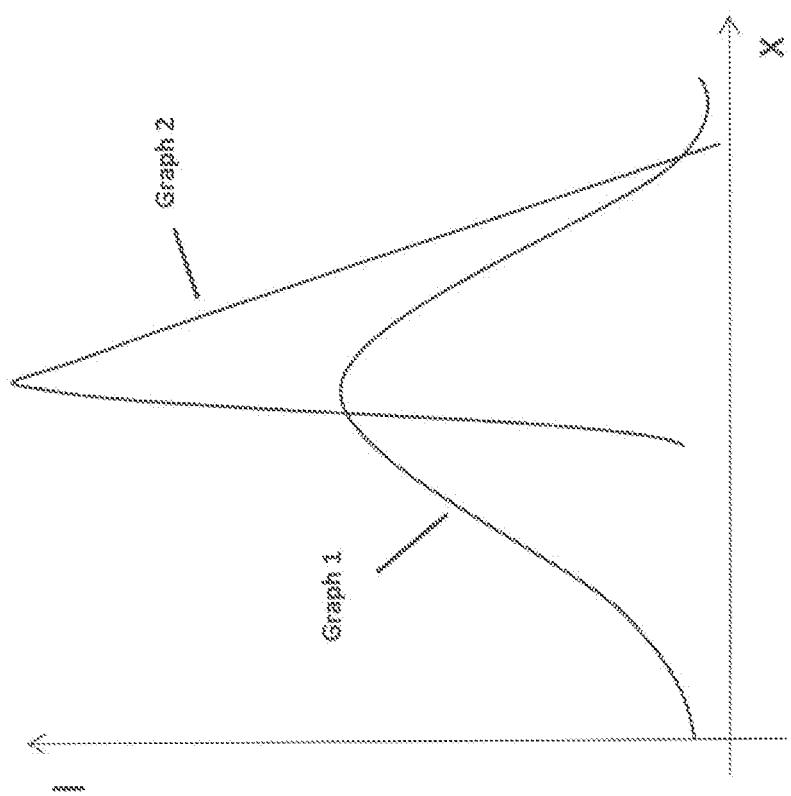
FIG. 14 is a graph illustrating an output signal of the sensor of FIG. 12 as a function of displacement of the liquid delivery system relative to the cap, compared to the output signal of a prior art optical sensor.

By way of example, turning to FIGS. 12-14, there is shown an implementation of optical sensor 110 according to one particularly preferred implementation in which optical emitter 111 and focusing element 114 direct a converging beam 115 obliquely inwards. For clarity of presentation, all components of cap 100 other than the optical elements have been omitted from this schematic illustration, but it will be understood that the optical sensor components are all rigidly mounted within the cap so as to move relative to the pen injector 200 during capping and uncapping. The oblique angle illustrated here is chosen to have an inclination towards the open end of cap 100, for illuminating the front side of plunger 220 through the fluid filled reservoir. This inclination is advantageous for allowing detection of plunger position even when the plunger is located near the beginning of its range of motion in cases where it lies within a non-transparent part of the pen-injector housing. A reverse inclination, deployed for sensing reflection from a rear surface of the plunger, may also be useful as an additional, or alternative, sensor in certain cases.

In the particularly preferred implementation illustrated here, optical emitter 111 and focusing element 114 are deployed such that converging beam 115 reaches its focal point after traversing a majority of a width of the transparent cylinder, and preferably so that focal point 116 lies at or near a wall of transparent cylinder 210, as shown in FIG. 12. In this context, "at or near the wall" refers to locations which are within a peripheral 10%, and more preferably within a peripheral 5%, of a cylindrical profile of cylinder 210 as measured along a diameter transverse to the central axis. Most preferably, focal point 116 lies substantially on an inner surface of transparent cylinder 210, as shown. The effect of this geometrical arrangement as the transparent cylinder 210 of the pen injector advances along the bore of the cap is illustrated in the sequence of FIGS. 13A-13C. In FIG. 13A, before plunger 220 intersects beam 115, the beam impinges on the wall of transparent cylinder 210 at a location relatively far from receiver 112, resulting in absorption of much of the illumination, with only low intensity scattering reaching receiver 112. As the pen injector advances in the direction illustrated by arrow 117 relative to the cap-mounted optical sensor 110, a leading edge of plunger 220 cuts beam 115 at or near focal point 116. Due to the converging geometry of beam 115, the beam has a very small cross-section, ideally approaching a "point" at focal point 116. As a result, there is an abrupt transition in reflected intensity from a minimum value to a maximum value corresponding to a very small movement as the edge of plunger 220 cuts beam 115, as shown in FIG. 13B. Further motion of the pen injector in direction 117 beyond this position typically results in a more gradual change in the intensity reaching received 112, typically slowly reducing as the converging beam 115 is progressively cut at a position further from the focal point, where the beam is more diffuse. The resulting signal intensity I obtained by receiver 112 as a function of displacement X along the capping motion is shown as Graph 2 in FIG. 14. The abrupt increase in signal facilitates accurate determination of when plunger 220 reaches a certain known spatial relation to optical sensor 110, thereby facilitating accurate overall measurements of plunger position within the reservoir and consequently dosing information. This contrasts to the more gradual variation in signal that is typically generated by an arrangement such as that of FIGS. 6A and 6B, represented here by Graph 1 of FIG. 14.

Figure 6A:
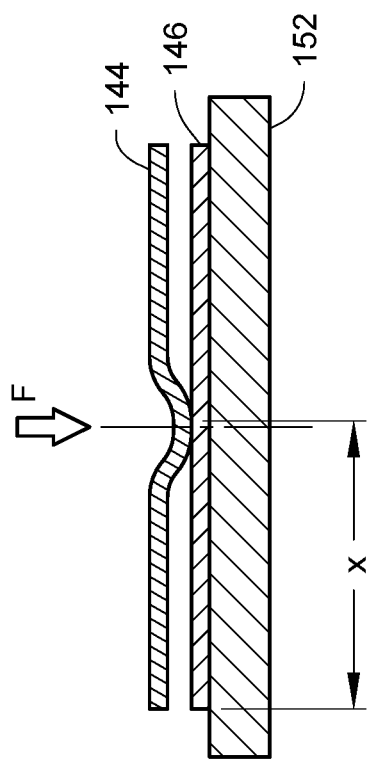
FIGS. 6A and 6B are schematic illustrations of the effect of smaller and larger contact pressure, respectively, on a region of electrical contact between layers of the linear potentiometer strip of FIG. 4A.
Figure 6B:
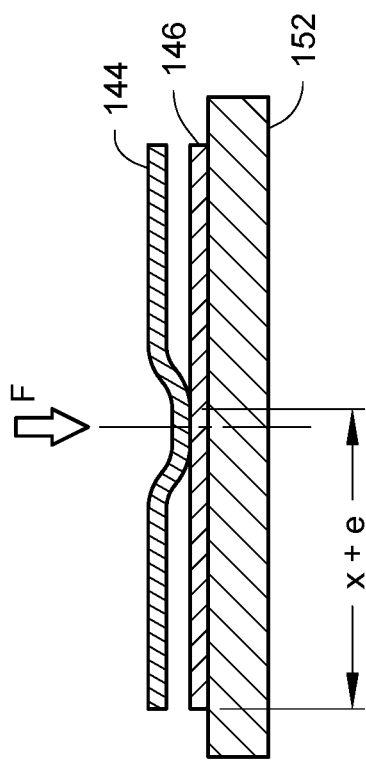
Figure 5:
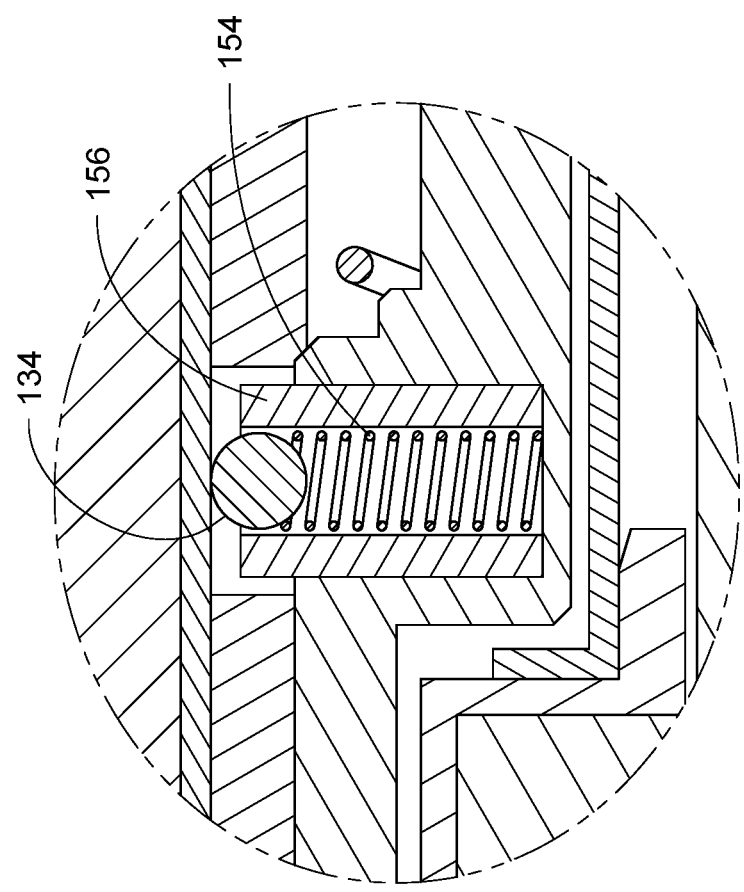
FIG. 5 is an enlarged view of a region of FIG. 3A identified by a circle designated V.
Figure 7A:
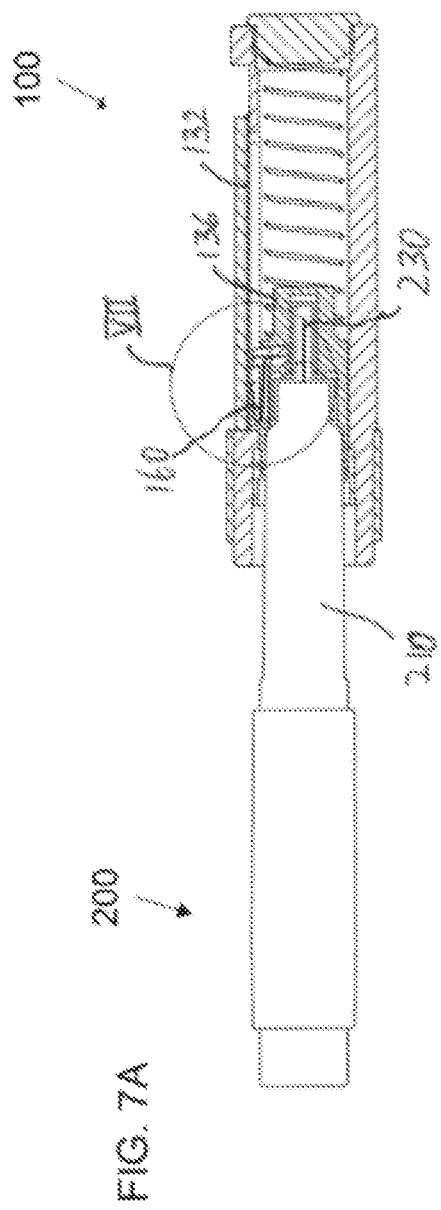
FIG. 7A is a view similar to FIG. 3A illustrating an alternative implementation of the position sensor employing a leaf spring pressure element.
Figure 7B:
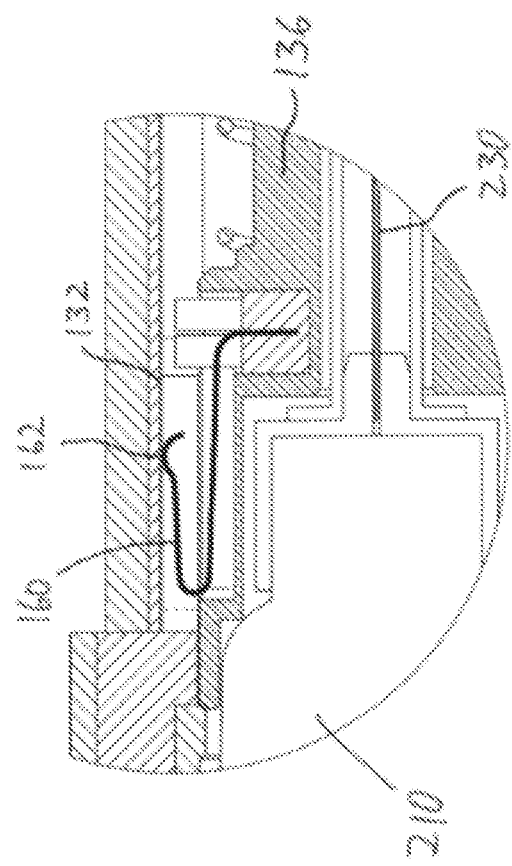
FIG. 7B is an enlarged view of a region of FIG. 7A identified by a circle designated VII.

Although the geometry of FIGS. 12 and 13A-13C has been illustrated here in a particularly preferred combination with focusing element 114, it should be noted that an implementation of this arrangement without a focusing element, for example, using a roughly parallel illumination beam or relatively narrow width, may also provide advantageous improvement compared to prior art arrangements such as that of FIG. 6A.

FIGS. 15A and 15B illustrate a further implementation of optical sensor 110 employing focusing element 114, in this case where the converging beam 115 is directed in a plane substantially perpendicular to the axis of transparent cylinder 210. "Substantially perpendicular" is used here to refer to angles that are within ±20 degrees from the perpendicular, and most preferably within about ±10 degrees from perpendicular. In the particularly preferred case illustrated here, both emitter 111 and receiver 112 are located in the same quadrant around the axis of the cylinder for operating in a reflection sensing mode. Here too, optical emitter 111 and focusing element 114 are preferably deployed such that converging beam 115 reaches its focal point at or near a wall of transparent cylinder 210, but in this case, the focal point 116 is at or near the internal surface of a region of the cylinder wall closest to optical emitter 111.

Operation of this embodiment of sensor 110 is best understood by comparing FIGS. 15A and 15B. In FIG. 15A, prior to plunger 220 intersecting converging beam 115, there is a small amount of back-scattering from the surfaces of transparent cylinder 210, of which some reaches receiver 112, but the transmitted light reaching the inside of transparent cylinder 210 diverges beyond the focal point, and is mostly scattered and dispersed, with very little reaching receiver 112. As the edge of plunger 220 cuts beam 115, there is a sudden increase in reflected intensity as the light traversing the inside wall of the cylinder is reflected from the surface of the plunger. Here too, since plunger 220 cuts beam 115 at or near focal point 116, the transition in reflected signal is abrupt, facilitating precise measurements.

In the case of a pen injector with a transparent cylindrical reservoir without optical obstructions, optical sensor 110 can essentially be implemented as a single emitter/receiver pair 111, 112 according to one of the configurations described above. In certain cases, however, commercially available pen injectors have various structural supporting and/or protecting structures which partially obscure surfaces of the transparent cylinder. Particularly for such applications, it may be desirable to implement cap 100 with one or more optical sensor with an oblique beam angle as per FIG. 12, optionally together with one or more optical sensor with a perpendicular beam orientation as per FIG. 15A, optionally axially spaced within cap 100, thereby providing sufficient information to address the various types of optical occlusions that may limit visibility of the leading and/or trailing end of plunger 220 as viewed at various different angles for various plunger positions.

By way of example, one type of obscuration in certain commercially available pen injectors is created by a plastic supporting structure overlying two opposing regions of cylinder wall 211 and extending along the cylinder parallel to its axis. In this case, a single emitter/receiver pair optical sensor would be at risk of failing to sense the plunger, depending on the orientation in which the pen injector is inserted into the cap. According to one option (not shown), features formed in cap 100 complementary to asymmetric supporting structure features of pen injector 200 may ensure orientation of the cap relative to the pen injector in one of the orientations in which the emitter/receiver pair are aligned with the exposed regions of transparent wall 211, without being obscured by supporting structure 212. According to an alternative optional solution, optical sensor 110 is implemented with two or more optical emitters 111 spaced around the central bore and a corresponding plurality of optical receivers 112 spaced around the central bore. As a result, no matter what orientation the pen injector is inserted into the cap, at least one pair of optical emitter and optical receiver are unobstructed. Where multiple pairs of emitters/receivers are located at a single axial position along the central bore, they may be treated for subsequent processing tasks as a single sensor used to generate a single output. According to one particularly preferred option, the single output is generated through a preprocessing step performed by processing system 122 according to which the emitter/receiver pair with the largest dynamic range in its output is selected as the "active" part of the sensor, and the smaller-dynamic-range pair(s) is ignored. Other options, such as summing the outputs of the sensors, may also provide effective results, but are believed to afford less sensitivity than the selective use of the highest-dynamic-range output.

In certain commercially available pen injectors, there exist a further type of optical obstruction in which longitudinal supporting structures are supplemented by a number of bridging ribs subdividing the window to the reservoir so as to form a number of fixed optical obstructions spaced along the transparent cylinder. The position of a leading surface of plunger 220 can be optically sensed when it is opposite a "window" between these ribs, but in certain positions, the leading surface is obscured from view by one or other of the ribs. This type of obscuration can be addressed by using the sensors to detect both the front and rear ends of plunger 220, in order to derive additional information for use to determine plunger position when the plunger is partially obscured. This approach requires additional algorithms based on prior measurements of the location of the ribs in order to assess which detected transitions correspond to ribs and which correspond to plunger extremities, and to switch between tracking plunger position according to the front or the rear surface position. Optionally, where locations of both the front and rear edges of the plunger are detected, both measurements may be used to improve precision and/or for error checking. Whenever the position of either the front or the back edge is in proximity to an obstruction, the processing system switches to the use of the unobstructed edge only. Additionally, or alternatively, according to certain implementations of the present invention, at least one radially-directed sensor such as that of FIG. 15A is combined with at least one obliquely directed sensor such as that of FIG. 12, such that obscuring of the beam by the ribs occurs at different plunger positions for the two sensors.

In certain commercially available pen injectors, a position of the plunger during its initial stages of motion is recessed within an opaque region of the pen injector housing, and only reaches the exposed transparent part of the reservoir after a period of use. The obliquely angled illumination beam of the optical sensor of FIG. 12 is ideal for sensing the plunger position in such cases.

The emitter may include a light source operating at any desired wavelength of visible or invisible light. In various embodiments in which more than one optical sensor is used, cross-talk between the sensors may be avoided either by use of distinct wavelengths for each sensor (with receivers also rendered wavelength-specific, for example, by addition of a bandpass filter), or by time-division multiplexing in which each sensor emits and senses pulses of illumination in distinct time periods of a cycle. Sampling rates are preferably at least 100 Hz, and typically in excess of 1000 Hz, rendering the sampling quasi-continuous relative to the rate of change of position during the capping or uncapping motions.

It should be noted that, in some cases, it may be possible to find wavelengths of illumination for the various optical sensors of the present invention which pass through various plastic parts of the device which are opaque to visible light. Thus, for example, it has been found that a beam of a solid state laser at 850 nm passes relatively unimpeded through the plastic support structures of various pen injectors, while be strongly attenuated by the silicone plunger of the devices. One non-limiting example of a suitable optical emitter for such a case is the vertical cavity surface emitting laser OPV382 commercially available from OPTEK Technology Inc. (US).

ADDITIONAL SYSTEM FEATURES

It is a particularly preferred feature of certain embodiments of the present invention that apparatus 100 is automatically actuated to take dosage readings once per dosing cycle, but assumes a low-power "sleep" state when not in use. A number of options may be used to achieve the automatic actuation. These include, but are not limited to, deployment of a microswitch 180 to activate the device, triggered for example by motion of 136 (moving with pen injector 200). Processing system 122 is responsive to the change of state of switch 180 to activate the device to its measuring mode, with all sensors actuated in their normal manner for measurement. Positioning of the microswitch can be chosen according to the intended mode of operation, triggered either at the beginning of a capping motion or at the beginning of uncapping, or possibly both. In each case, the device is preferably configured to return to a low-power sleep mode after a given time period sufficient to complete the capping or uncapping motion, which is typically not more than a few seconds. Optionally, subsets of components may be deactivated at different times, according to their functions, with the sensors being deactivated only sufficient time to complete the capping/uncapping movement and associated measurements, while the processing and display components may remain active for longer to complete all necessary calculations and to display the results for a predefined period of time. A button 131 is typically provided to reactivate the display 130 on demand to display the most recent dosage data.

In an alternative implementation for achieving power-up from a sleep state without a mechanical microswitch, linear potentiometer 132 may itself be used in a low-power mode as an actuation input, for example, assuming an extreme position in which no electrical contact occurs between the layers and employing the electrical contact as an power-up input.

Referring briefly to the remaining components illustrated in FIG. 1, it will be appreciated that processing system 122 includes at least one processor 124 and a data storage device 126, preferably as well as communications subsystem 140. It will be appreciated that processing system 122 may be implemented in various ways, using standard processor chips suitably configured by software, or firmware, or by use of dedicated hardware, or any combination thereof, all in combination with suitable input and output interfaces required for driving and receiving outputs from the various sensors and other components of the system. Display 130 is typically a display of a limited number of digits or alpha-numeric information, which typically displays the last delivered dosage and the time at which that dosage was delivered. For more extensive information, display of historical records and/or analysis of drug delivery patterns, data is preferably uploaded via communications subsystem 140, which may be a wireless communications subsystem according to any desired standard, such as Bluetooth, or a wired connection interface, such as a micro-USB connector, to an external electronic device. The external device may be a user device such as a personal computer (PC) or a mobile communications device (smartphone), or an Insulin pump and/or glucose monitoring device. The device may be running diabetic management software (e.g., an APP). Additionally or alternatively, the data may be transferred to a network-connected system of a healthcare provider. The may provide additional information, either directly or via an external device, including a history of the injections for a predetermined period of the time, and alert indications on empty cartridge, near empty cartridge, scheduled time for an injection, etc.

The entire apparatus is powered by a power source 128, which may typically be a number of miniature batteries, such as button-cells, which may be single-use or rechargeable cells.

At this stage, the operation of the various embodiments of the present invention, and a corresponding method according to the present invention, will be clear. Specifically, the various implementations detect the plunger position based on signals sampled during relative motion while the pen injector is being uncapped or recapped. The current plunger position is compared to the previously measured plunger position to determine whether a dose of drug has been administered and, if so, what dosage quantity. The cap then generates a display, typically on display panel 130, which indicates the time and quantity of the last dose delivered.

Although the present invention has been exemplified in the context of a pen injector, variant implementations of the present invention may be used to determine dosage delivered and/or remaining quantity in any context in which a drug or other liquid is delivered by a syringe-type device.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. An apparatus for use with a liquid delivery system, the liquid delivery system including a transparent cylinder for housing a liquid and an at least partially opaque plunger movable along an axis of the cylinder for expelling the liquid through an outlet, the apparatus comprising:

(a) a sliding cover configured for sliding engagement with the cylinder so as to be slidable along the cylinder parallel to the axis from a first position to a second position;

(b) a set of sensors housed in said sliding cover so as to move together with said sliding cover, said set of sensors comprising:
  (i) an optical sensor having an optical emitter for emitting radiation and an optical receiver for generating a first output indicative of an amount of said radiation received by said optical receiver, said optical sensor further comprising a focusing element deployed in relation to said optical emitter so as to generate a converging beam of radiation converging towards a focal point, said converging beam being directed inwards, and
  (ii) a position sensor operating independently from the optical sensor and deployed for generating a second output indicative of a current position of said sliding cover between said first position and said second position; and (c) a processing system associated with said set of sensors so as to receive at least said first output and said second output, said processing system being configured to be responsive to a variation in said first output indicative of said optical sensor reaching a known spatial relationship to the plunger.

2. The apparatus of claim 1, wherein said optical sensor directs said converging beam obliquely inwards.

3. The apparatus of claim 1, wherein said focusing element comprises a refractive lens.

4. The apparatus of claim 1, wherein said optical emitter and said focusing element are deployed such that said converging beam reaches said focal point after traversing a majority of a width of the transparent cylinder.

5. The apparatus of claim 1, wherein said focal point lies at or near a wall of the transparent cylinder.

6. The apparatus of claim 1, wherein said sliding cover is implemented as a cap with a central bore for receiving an end portion of a pen injector having a projecting needle.

7. The apparatus of claim 6, further comprising a cradle slidingly mounted within said central bore, said cradle configured for receiving the end portion of the pen injector, said cradle being spring biased towards an end position for engaging the end portion of the pen injector when said sliding cover is in said first position, and being retractable to move together with the end portion of the pen injector as said sliding cover slides to said second position.

8. The apparatus of claim 7, wherein said position sensor is associated with said cradle so that said second output is indicative of a current position of said cradle within said central bore.

9. The apparatus of claim 8, wherein said position sensor comprises a linear potentiometer strip deployed within said cap so as to extend parallel to said axis, and a pressure element mounted to said cradle and biased so as to press against said linear potentiometer strip.

10. The apparatus of claim 9, wherein said pressure element comprises a spring-loaded ball.

11. The apparatus of claim 9, wherein said pressure element comprises a leaf spring mounted to said cradle, said leaf spring providing a protuberance deployed so as to press against said linear potentiometer strip.

12. The apparatus of claim 11, wherein said leaf spring is implemented as a folded cantilever leaf spring, and wherein said folded cantilever leaf spring comprises a first elongated segment anchored to said cradle, and a second elongated segment connected to said first elongated segment via a bend region, wherein said protuberance is provided on said second elongated segment, said first and second elongated segments and said bend region being configured so accommodate radial displacement of said protuberance towards said cradle without generating axial displacement of said protuberance relative to said cradle.

13. An apparatus for use with a pen injector, the pen injector including a transparent cylinder for housing a liquid and an at least partially opaque plunger movable along an axis of the cylinder for expelling the liquid through an outlet, the apparatus comprising:

(a) a cap with a central bore extending along an axis, said cap configured for sliding engagement with the cylinder so as to be slidable along the cylinder parallel to the axis from a first position to a second position;

(b) a cradle slidingly mounted within said central bore, said cradle configured for receiving an end portion of the pen injector, said cradle being spring biased towards an end position for engaging the end portion of the pen injector when said cap is in said first position, and being retractable to move together with the end portion of the pen injector as said cap slides to said second position;

(c) a set of sensors housed in said cap so as to move together with said cap, said set of sensors comprising:
  (i) an optical sensor having an optical emitter for emitting radiation and an optical receiver for generating a first output indicative of an amount of said radiation received by said optical receiver, and
  (ii) a position sensor deployed for generating a second output indicative of a current position of said cradle within said central bore; and (d) a processing system associated with said set of sensors so as to receive at least said first output and said second output, said processing system being configured to be responsive to a variation in said first output indicative of said optical sensor reaching a known spatial relationship to the plunger, wherein said position sensor comprises a linear potentiometer strip deployed within said cap so as to extend parallel to said axis, and a pressure element mounted to said cradle and biased so as to press against said linear potentiometer strip.

14. The apparatus of claim 13, wherein said pressure element comprises a spring-loaded ball.

15. The apparatus of claim 13, wherein said pressure element comprises a leaf spring mounted to said cradle, said leaf spring providing a protuberance deployed so as to press against said linear potentiometer strip.

16. The apparatus of claim 15, wherein said leaf spring is implemented as a folded cantilever leaf spring, and wherein said folded cantilever leaf spring comprises a first elongated segment anchored to said cradle, and a second elongated segment connected to said first elongated segment via a bend region, wherein said protuberance is provided on said second elongated segment, said first and second elongated segments and said bend region being configured so accommodate radial displacement of said protuberance towards said cradle without generating axial displacement of said protuberance relative to said cradle.

17. The apparatus of claim 13, wherein said optical sensor further comprises a focusing element deployed in relation to said optical emitter so as to generate a converging beam of radiation converging towards a focal point, said converging beam being directed obliquely inwards.

18. The apparatus of claim 17, wherein said focusing element comprises a refractive lens.

19. The apparatus of claim 17, wherein said optical emitter and said focusing element are deployed such that said converging beam reaches said focal point after traversing a majority of a width of the transparent cylinder.

20. The apparatus of claim 19, wherein said focal point lies at or near a wall of the transparent cylinder.

* * * * *